United States Patent [19]

Lee et al.

[11] Patent Number: 5,489,681

[45] Date of Patent: Feb. 6, 1996

[54] METHOD FOR THE PREPARATION OF 4-PHENYL-1,3-BENZODIAZEPINS

[75] Inventors: Thomas B. K. Lee, Whitehouse Station; George E. Lee, Somerville, both of N.J.

[73] Assignee: Hoeschst-Roussel Pharmaceuticals, Inc., Somerville, N.J.

[21] Appl. No.: 304,662

[22] Filed: Sep. 9, 1994

Related U.S. Application Data

[62] Division of Ser. No. 980,449, Nov. 23, 1992, Pat. No. 5,349,086, which is a continuation of Ser. No. 870,772, Apr. 21, 1992, abandoned, which is a continuation of Ser. No. 737,610, Jul. 29, 1991, abandoned, which is a continuation of Ser. No. 579,262, Sep. 7, 1990, abandoned, which is a continuation of Ser. No. 384,115, Jul. 21, 1989, abandoned, which is a continuation of Ser. No. 98,210, Sep. 18, 1987, abandoned, which is a division of Ser. No. 757,765, Jul. 23, 1985, Pat. No. 4,709,093, which is a continuation of Ser. No. 267,990, May 28, 1981, abandoned.

[51] Int. Cl.[6] .................... C07D 243/204; A61K 31/55
[52] U.S. Cl. ........................................................ 540/567
[58] Field of Search ............................................. 540/567

[56] References Cited

U.S. PATENT DOCUMENTS

| | | | |
|---|---|---|---|
| 3,510,560 | 5/1970 | Saunders | 424/330 |
| 4,309,424 | 1/1982 | Martin et al. | 424/244 |
| 5,292,760 | 3/1994 | Martin et al. | 540/567 |

OTHER PUBLICATIONS

Muchowski et al. "Ortho Functionalization of N–(t–butoxycarbonyl)aniline," JOC 45:4798–4801 (1980).
Fuhrer et al., "Ortho Functionalization of Aromatic Amines: Ortho lithiation of N–Pivaloylanilines," JOC 44:1133–1136 (1979).
Muchowski et al., "O–Functionalization of Aromatic Amines: O–Lithiatian of N–Povaloylanilines," JOC 44:1133–1136 (1979).

Primary Examiner—Robert T. Bond

Attorney, Agent, or Firm—Finnegan, Henderson, Farabow, Garrett, & Dunner

[57] ABSTRACT

A compound of the formula

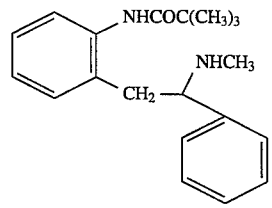

(II)

is prepared by reacting an N-acylated-o-toluidine of the formula

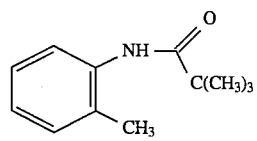

(III)

with n-alkyllithium to form a dilithio intermediate of the formula

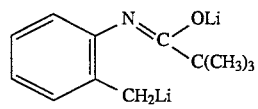

(IV)

which can then be quenched with N-benzylidenemethylamine to fore compound II. Hydrolysis of compound(II) yields the free base

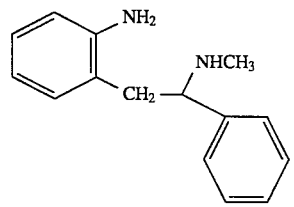

(V)

or its salt, which can be cyclized to form 4,5-dihydro-2,3-dimethyl-4-phenyl-3H-1,3-benzodiazepine or its physiologically acceptable salts, which are useful as pharmacological agents.

9 Claims, No Drawings

METHOD FOR THE PREPARATION OF 4-PHENYL-1,3-BENZODIAZEPINS

This is a division of application Ser. No. 07/980,449, filed Nov. 23, 1992 Pat. No. 5,349,086, which is a continuation of Ser. No. 07/870,772, filed Apr. 21, 1992, which is a continuation of Ser. No. 07/737,610 filed Jul. 29, 1991, which is a continuation of Ser. No. 07/579,262, filed Sep. 7, 1990, which is a continuation of Ser. No. 07/384,115, filed Jul. 21, 1989, which is a continuation of Ser. No. 07/098,210, filed Sep. 18, 1987, which is a divisional of Ser. No. 06/757,765, filed Jul. 23, 1985 Pat. No. 4,709,093, which is a continuation of Ser. No. 06/267,990, filed May 28, 1981.

The present invention relates to a method for the preparation of 4-phenyl-1,3-benzodiazepines, and in particular to the compound 4,5-dihydro-2,3-dimethyl-4-phenyl-3H-1,3-benzodiazepine, and its optical antipodes and physiologically acceptable salts.

The compound 4,5-dihydro-2,3-dimethyl-4-phenyl-3H-1,3-benzodiazepine has the formula

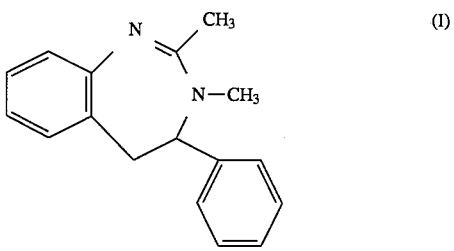

This compound, its optical antipodes and physiologically acceptable salts are useful as antidepressants, analgetics and anticonvulsants. Of particular interest for these purposes are the hydrochloride salts of the 4-phenyl-1,3-benzodiazepine of formula (I).

The 4-phenyl-1,3-benzodiazepines, methods for their preparation and compounds useful as intermediates in their preparation are known. The known methods of preparation require a relatively large number of steps, the steps are relatively complicated, the starting materials are costly and the yields of the 4-phenyl-1,3-benzodiazepines are less than desirable. Thus, there exists a need in the art for a new process for the preparation of the 4-phenyl-1,3-benzodiazepines.

Accordingly, this invention aids in fulfilling this need by providing a process utilizing more economical starting materials and a relatively small number of uncomplicated steps. The 4-phenyl-1,3-benzodiazepines are obtained in high yields and increased purity. This invention also provides a novel intermediate compound utilized in the process of this invention. This intermediate has the formula

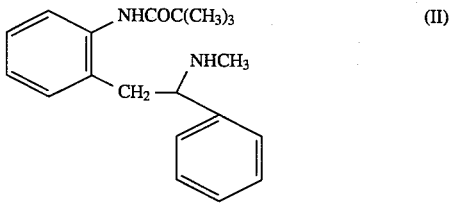

and the chemical name N-[2-(2-methylamino-2-phenylethyl)phenyl]-2,2-dimethylpropanamide.

The compounds of formula (I) and the compounds of formula (II) can be prepared according to the following sequence of reactions.

1. An n-acylated-o-toluidine of the formula

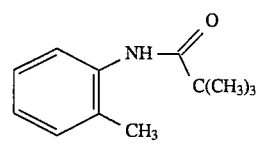

is converted to a dilithio intermediate of the formula

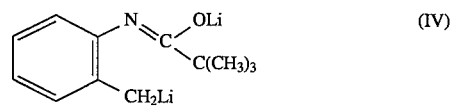

The N-acylated-o-toluidine of formula (III) is N-[(2-methyl)phenyl]-2,2-dimethylpropanamide. Lithiation of aromatic compounds with an n-alkyllithium compound is exemplified in J.M. Muchowski and M. Venuti, J. Org. Chem. 45, 4798–4801 (1980) and W. Fuhrer and H. W. Gschwend, J. Org. Chem. 44, 1133–1136 (1979). A preferred method according to the present invention involves slowly adding a solution of n-butyllithium in a solvent therefor, such as hexane, to a solution of the N-acylated-o-toluidine in an ethereal solvent, such as diethyl ether, tetrahydrofuran, dimethoxyethane, and a hydrocarbon solvent, such as hexane. The ethereal solvent and hydrocarbon solvent should be substantially inert to the n-butyllithium to avoid adverse side reactions. The temperature during the addition can range from about 14°–70° C. to about 30° C., preferably about −10° C. to about 30° C. The resulting mixture is aged from about one-half to about 5 hours, preferably about 1 to about 2 hours The reaction is conveniently carried out at atmospheric pressure. The amount of n-butyllithium employed is up to about 10% in excess of the 2 molar equivalents required for the reaction. It is important to exclude moisture from the reaction mixture. Accordingly, the reaction is conveniently conducted in an atmosphere of a substantially dry gas, such as substantially anhydrous nitrogen.

2. The dilithio intermediate of formula (IV) is quenched with N-benzylidenemethylamine to provide the N-[2-(2-methylamino-2-phenylethyl) phenyl]-2,2-dimethylpropanamide of formula (II). N-Benzylidenemethylamine and a method for its preparation are disclosed by R. B. Moffett et al, Org. Syn. Coil., Vol. IV, 605–608 (1963). The temperature of addition of the N-benzylidene-methylamine can range from about −78° C. to about 35° C., preferably from about 0° to about 25° C. The mixture is aged for a period of about 5 minutes to about one hour. The amount of N-benzylidene-methylamine employed is from about one to about 2 molar equivalents based on the dilithio intermediate of formula (IV). The quenching is conveniently conducted at atmospheric pressure and in a substantially moisture-free, e.g., dry nitrogen, atmosphere.

3. The propanamide of formula (II) is then hydrolyzed to provide an N-methyl-2-amino-α-phenylphenethylamine as a free base of the formula

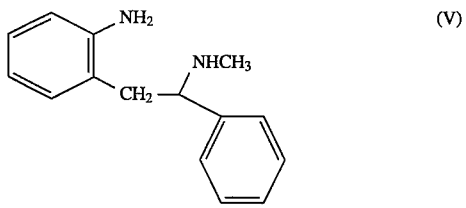

or as its salt, e.g. dihydrochloride. The aromatic amine of formula (V) is the immediate precursor of the 4-phenyl-1,3-benzo-diazepines of formula (I). Thus, it will be understood that the salts of the compound of formula (V) can in general be the same as the salts of the compounds of formula (I). In one method the compound of formula (II) is reacted with about 2 molar equivalents of a strong mineral acid, such as hydrochloric acid, hydrobromic acid or sulfuric acid. 6N Hydrochloric acid is the acid of choice. The reaction is conveniently conducted at atmospheric pressure and at a temperature of from about. 70° to the reflux temperature of the solvent employed in the reaction for a period of about 12 to about 48 hours to provide a diacid salt, which can then be recrystallized. A solvent, such as ether or an aromatic solvent, is employed to remove any side products while retaining the diacid salt in aqueous phase. If desired, the diacid salt can be basified to provide the free base.

4. The aromatic amine of formula (V) in free base or salt form can be cyclized with a compound of the formula

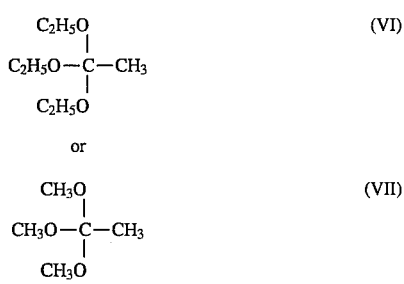

to provide the 4-phenyl-1,3-benzodiazepines of formula (I). This cyclization can be carried out in the presence of an acid catalyst, such as ethanotic-hydrochloric acid. Alternatively, the monoacid or diacid salt of the compound of formula (V) can be cyclized with a compound of formula (VI) or formula (VII) in a polar solvent, such as acetonitrile or acetic acid; this makes it unnecessary to add an acid catalyst to the reaction mixture. The reaction can be conducted at a temperature of from about 23° C. to the reflux temperature of the reaction mixture and at atmospheric pressure for at least about 1 hour, typically about 1 to about 8 hours. About 1 to about 5 molar equivalents of the compound of formula (VI) or formula (VII) are employed.

The invention is described in greater detail in the following examples in which all parts, proportions, ratios and percentages are by weight unless otherwise indicated.

Example 1

Synthesis of trimethylacetyl chloride

A solution of trimethylacetic acid (204.3g, 2.0 mol) in imethylene chloride (400 ml) containing a catalytic amount of DMF (0.5g) was stirred under a dry nitrogen atmosphere and treated with $SOCl_2$ (258g, 2.06 mol). Following the addition of $SOCl_2$ (about 5 minutes) the reaction temperature dropped from 21° C. to 13° C.; at the same time, a vigorous evolution of HCl and $SO_2$ occurred. After 5 hours, the reaction was heated to reflux and maintained at this temperature for 2 hours. At this time, the conversion of trimethylacetic acid to trimethylacetyl chloride was quantitative. The crude product, without concentration or distillation, can be employed directly in the synthesis of N-[(2-methyl) phenyl ] -2,2-dimethyl propanamide.

Example 2

Synthesis of N-[(2-methyl)phenyl]-2,2-dimethyl propanamide (a) A biphasic solution of o-toluidine (107.2g, 1.0 mol) in methylene chloride (500 ml) and water (150 ml)-containing sodium carbonate (69g, 0.65 mol) was treated with trim- ethylacetyl chloride (120.6g, 1.0 mol). The rate of addition of trimethylacetyl chloride was adjusted so as to maintain the reaction at gentle reflux. After 45 minutes the addition was complete. The organic layer was separated, washed with water, and concentrated in vacuo. The crude N-[(2-methyl)phenyl]-2,2-dimethylpropanamide was slurried in 2% aqueous HCl, filtered and washed with $H_2O$ until the filtrate was neutral. After drying in vacuo (50° C., 20 ram), N-[(2-methyl)phenyl]-2,2-dimethylpropanamide (178 g, 0.93 mol) was obtained in 93% yield. (top 109°–110° C.).

(b) A biphasic solution of o-toluidine (214.4g, 2.0 tool) in methylene chloride (200 ml) and water (250 ml) containing sodium carbonate (117g, 1.1 mol) was treated with trimethylacetyl chloride (about 2.0 mol in methylene chloride from Example 1). The addition of trimethylacetyl chloride was complete after 50 minutes; the temperature ranged between 37°–50° C. during the addition. The warm organic phase was separated and the aqueous phase was-extracted with methylene chloride (2×100 ml). The combined methylene chloride solution was washed with 1N HCl (2×100 ml), $H_2O$ (3×200 ml), 10% NaCl (100 ml), and concentrated in vacuo (<25° C. at 30 ram) to give free flowing crystalline N-[(2-methyl)phenyl]-2,2-dimethylpropanamide. Final drying at (60° C., 30 mm, 24 hrs) gave N-[(2-methyl)phenyl]-2,2-dimethylpropanamide (379g, 1.98 mol) in 99% yield. The melting point of the product was 108°–111° C. This product can be used directly in Example 4(b) without recrystallization.

Example 3

Synthesis of N-Benzylidenemethylamine (a) Anhydrous monomethylamine (about 1–1.5 eq,) was introduced below the surface of a stirred solution of benzaldehyde (1062 g, 10.0 mol) in toluene (2000 ml) cooled to 0° C. The rate of addition of monomethylamine was adjusted so as to maintain the reaction temperature between 25°–30° C.; after 45 minutes the addition of monomethylamine was terminated. The organic phase was separated and concentrated in vacuo. Distillation of the residual oil afforded N-benzylidenemethylamine (1047g, 8.79 mol) in 88% yield. The product had a boiling point of 79° C. at 20 mm. [This N-benzylidinemethylamine starting material is reported by R. B. Moffett et al, Org. Syn. Coll. Vol. IV, 605–608 (1963)].

(b) Anhydrous monomethylamine (about 1–1.5g) was bubbled into a stirred solution of benzaldehyde (531g, 5.0 mol) in toluene (1000 ml) at 0° C. The rate of addition of monomethyl amine was adjusted so as to maintain the reaction temperature between 20°–25° C. The progress of the reaction was evaluated by GC [using a 6'-2 mm, 3% OV-101 (silicone polymer) on 80/100 mesh Chromosorb W Column.] After 30 minutes, monomethylamine addition was stopped; at 50 minutes into the reaction the conversion of benzaldehyde to N-benzylidinemethylamine was 99%. At this point, the aqueous phase was separated and the toluene phase was concentrated in vacuo (50°–60° C. at 30 mm) to give a colorless to pale yellow oil (657g). This crude oil was shown by NMR and GC to contain 76% N-benzylidinemethylamine and 24% toluene. The conversion to N-benzylidinemethylamine was greater than 99.7% by GC. The calculated yield of N-benzylidinemethylamine was 84%. This crude product can be used in subsequent reactions without distillation.

Example 4

Synthesis of N-[2-(2-methylamino-2-phenylethyl)-phenyl]-2,2-dimethylpropanamide (a) A stirred solution of N-[(2-methyl)phenyl]-2,2-dimethylpropanamide (95.6g, 0.5mol) in THF (500 ml, dried over 4Å molecular sieves) was cooled to 0° C. and treated with 1.6M n-butyllithium in hexane (630 ml, 1.0 mol). The addition of n-butyllithium was complete after 45 minutes. During the addition, the temperature of the mixture was maintained below 10° C. with external cooling. The resultant dianion solution was aged (about 1–2 hrs) at 0° C. until the homogeneous orange solution became a white heterogeneous slurry. The dianion was then quenched with N-benzylidenemethylamine (63.7g, 0.6 mol) and aged for 30 minutes at 15°–25° C. The reaction mixture was diluted with ether (200 ml), treated with crushed ice (200g), and. stirred for 15 minutes. The organic phase was separated, washed with saturated sodium chloride, dried over anhydrous magnesium sulfate and concentrated in vacuo. The residual oil was crystallized from hexane (400 ml) at 5° C. to give N-[2-(2-methylamino-2-phenylethyl) phenyl]-2,2-dimethylpropanamide (121.2g, 0.39 mol) in 78% yield. The product had a melting point of 85°–86° C.

(b) A heterogeneous mixture of N-[(2-methyl)phenyl]-2,2-dimethylpropanamide (95.6g, 0.5 mol) and THF (200 ml) was stirred under a dry nitrogen atmosphere at 0°–10° C. The first equivalent of 1.6M n-butyllithium in hexane (305 ml) was rapidly added (about 5 min) causing the temperature to increase to 20° C. and at the same time causing a complete dissolution of starting material. (The end point for the first equivalent can be judged gravimetrically or by observance of a distinctive color change produced upon formation of trace amounts of the dianion). A second equivalent of 1.6M n-butyllithium in hexane (305 cc) was added and the dianion solution aged at 0°–5° C. for 1–2 hours. N-benzylidinemethylamine (89 cc) of a 76% solution in toluene containing 0.6 mol. was added causing the heterogeneous mixture to become homogeneous and bi-phasic (the resultant monoanion is immiscible when the ratio of the THF:hexane is decreased as in this Example). The biphasic solution was stirred for 30 minutes at 0°–5° C. then treated with $H_2O$ (300 ml). The organic phase was separated, dried over anhydrous sodium sulfate, filtered, and concentrated in vacuo (30 mm) at 45° C. to give a crystalline product. Recrystallization from cold hexane (300 ml) gave a N-[2-(2-methylamino-2-phenylethyl)phenyl]-2,2-dimethylpropanamide (118g, 0.38 mol) in 76% yield with a melting point of 85°–86° C.

Example 5

Synthesis of N-methyl-2-amino-α-phenylphenethyl-amine dihydrochloride (a) N-[2-(2-methylamino-2-phenylethyl)phenyl]-2,2-dimethyl-propanamide (62g, 0.2 mol) was dissolved in 6 N HCl (124g) and stirred under a nitrogen atmosphere at 100° C. for 24 hours. The warm reaction mixture (about 35°–40° C.) was extracted with toluene (2×100 ml) to effect recovery of trimethylacetic acid. The aqueous phase was dried by azeotropic distillation with toluene (200 ml) using a Dean-Stark phase separator. The product was collected by filtration, slurried in hot 2-propanol (200 ml), re-filtered and dried in vacuo (30 mm) at 45° C. for 12 hours to give N-methyl-2-amino-α-phenylphenethylamine dihydrochloride (58.7g. 0.196 mol) in 98% yield. The product had a melting point of 251°–253° C.

(b) N-[2-(2-methylamimo-2-phenylethyl)phenyl]-2,2-dimethyl-propanamide (155g, 0.5 tool) was dissolved in 6 N HCl (310g) and stirred under a nitrogen atmosphere at 100° C. for 28 hours. The reaction mixture was cooled to 23° C. and toluene (200 ml) was added. Stirring was continued until the product had crystallized from the aqueous phase. The product was collected by filtration, washed with toluene (2×50 ml) and dried in vacuo (30 mm) at 60° C. for 60 hours to give N-methyl-2-amino-α-phenylphenethyl-amine di-hydrochloride (139g, 93% yield). The melting point of the product was 252°–254° C. The organic phase of the filtrate was concentrated in vacuo to give a 58% recovery of trimethylacetic acid. The aqueous phase of the filtrate afforded a second crop of N-methyl-2-amino-α-phenethylamine dihydrochloride (9.3g, 6%) The total yield of product was 99%.

Example 6

Synthesis of 2,3-dimethyl-4-phenyl-3H-1,3-benzodi-azepine hydrochloride

A heterogeneous mixture of N-methyl-2-amino-α-phenylphen-ethylamine dihydrochloride (150g, 0.5 mol) in acetonitrile (500 ml) was treated with triethylorthoacetate (202 ml, 1.1 mol) and heated to 70° C. for 2 hours with stirring under a dry nitrogen atmosphere. The reaction mixture was filtered, concentrated in vacuo, and the residual solid recrystallized from 2-propanol at –10° C. to give 2,3-dimethyl-4-phenyl-3H-1,3-benzodiazepine hydrochloride (118g, 0.413 mol) in 83% yield. The product had a melting point of 239.5°–241° C.

Example 7

Synthesis of 2,3-dimethyl-4-phenyl-3H-1,3-benzodi-azepine. (free base)

A heterogeneous mixture of the dihydrochloride salt of N-ethyl-2-amino-α-phenylphenethylamine (9g, 0.03 mol) in acetonitrileo (36 cc dried over 4Å molecular sieves) was treated with triethylorthoacetate (9.73g, 11 cc, 0.06 mol) and heated to 70° C. with stirring under a dry nitrogen atmosphere. At 50° C., (after about 15 minutes of heating) the reaction mixture became homogeneous. The reaction mixture was concentrated in vacuo and partitioned between 100 ml toluene and 50 ml 5% NaOH. The toluene phase was washed with 10% NAG1, dried over sodium sulfate, filtered and concentrated in vacuo to give a light yellow-brown solid product, which was shown by GC to be 96.7% 2,3-dimethyl-4-phenyl-3H-1,3-benzodiazepine This crude product free base was recrystallized from 15 ml 2-propanol at 82° C., diluted with 30 ml hexane and dried at 45° C. (30 mm for 12 hours). 4.64g (0.0185 mol) of product with a melting point of 144.5°–145.4° C. were obtained at a yield of 61.8%. A second crop was recrystallized from 5 ml 2-propanol, washed with 3 ml hexane and dried at 40° C. (30 mm for 12 hours), 1.92g (0.0077mol) of product with a melting point of 143.5°–144.5° C. were obtained at a yield of 25.6%. The mother liquor (0.64g) from the first crop contained 0.24g of product representing a yield of 3.2%.

Example 8

Conversion of 2,3-dimethyl-4-phenyl-3H-1,3-benzodiazepine (free base) to hydrochloride salt 1.9g (0.0759 mol) of the free base 2,3-dimethyl-4-phenyl-3 H-1,3-benzodiazepine obtained in Example 10 was dissolved in 2-propanol and treated at 5°–10° C. with an excess of 2-propanol saturated with anhydrous HC1. The monohydrochloride salt of the 2,3-dimethyl-4-phenyl-3H-1,3-benzodiazepine was recrystallized from solution and recovered by filtration. The monohydrochloride salt had a melting point of 241°–242° C. The salt was dried (60° C., 30 mm, 24 hours) to yield 1.50g of a white crystalline powder.

What is claimed:

1. A process for preparing 4,5-dihydro-2,3-dimethyl-4-phenyl-3 H-1,3-benzodiazepine or a pharmaceutically acceptable salt thereof, said process comprising (A) reacting N-[(2-methyl)phenyl]-2,2-dimethylpropanamide with n-alkyllithium to provide a dilithio intermediate of the formula

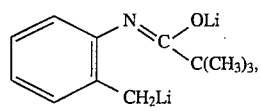

(B) quenching the dilithio intermediate with N-benzylidenemethylamine to form N-[2-(2-methylamino-2-phenylethyl)phenyl]-2,2-dimethylpropanamide.

(C) hydrolyzing the N-[2-(2-methylamino-2-phenymethyl) phenyl]-2,2-dimethylpropanamide to form N-methyl-2-amino-α-phenylphenethylamine as a free base or salt thereof, and (D) cyclizing said N-methyl-2-amino-a-phenylphenethylamine by reaction with a compound of the formula

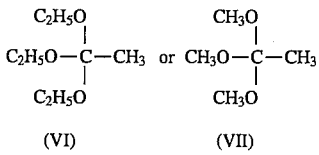

to form 4,5-dihydro-2,3-dimethyl-4-phenyl-3H-1,3-benzodiazepine or a pharmaceutically acceptable salt thereof.

2. Process according to claim 1 wherein cyclization is carried out with about 1 to about 5 molar equivalents of the compound of formula (VI) or the compound of formula (VII) for a time of about 1 to about 8 hours.

3. Process according to claim 2 wherein cyclization is carried out in the presence of acid catalyst.

4. Process according to claim 3 wherein cyclization is carried in the presence of ethanolic hydrochloric acid as acid catalyst.

5. Process according to claim 2 wherein cyclization is carried out in polar solvent and in the absence of acid catalyst.

6. Process according to claim 5 wherein the polar solvent is acetonitrile or acetic acid.

7. A process for preparing 4,5-dihydro-2,3-dimethyl-4-phenyl-3H-1,3-benzodiazepine or a pharmaceutically acceptable salt thereof said process comprising (A) reacting N-[(2-methyl)phenyl]-2,2-dimethylpropanamide with n-butyllithium in solution in tetrahydrofuran and hexane and in a substantially anhydrous atmosphere at about −10° C. to about 30° C. for about 1 to about 2 hours to form a dilithio intermediate of the formula

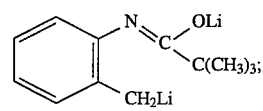

(B) quenching the dilithio intermediate with about 1 to about 2 molar equivalents of N-benzylidenemethylamine, based on the dilithio intermediate, at about 0° C. to about 25° C. for about 5 minutes to about 1 hour and in a substantially anhydrous atmosphere to form N-[2-(2-methylamino-2-phenylethyl)phenyl]-2,2-dimethyl propanamide;

(C) hydrolyzing the N-[2-(2-methylamino-2-phenylethyl) phenyl]-2,2-dimethylpropanamide by reaction in solution with an acid selected from the group consisting of hydrochloric acid, hydrobromic acid or sulfuric acid at about 70° C. to the reflux temperature of the solvent for a period of about 12 to about 48 hours; and (D) cyclizing said N-methyl-2-amino-α-phenylphenethylamine by reaction with about 1 to about 5 equivalents of a compound of the formula

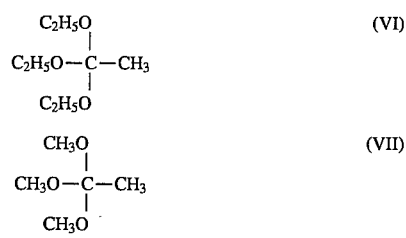

for a time of about 1 to about 8 hours to form 4,5-dihydro-2,3-dimethyl-4 -phenyl-3H-1,3-benzodiazepine or a pharmaceutically acceptable salt thereof.

8. Process according to claim 7 wherein a solution of the n-butyllithium is added to the N-[(2-methyl)phenyl]-2,2-dimethylpropanamide.

9. Process according to claim 7 wherein the acid in (C) is hydrochloric acid.

* * * * *

UNITED STATES PATENT AND TRADEMARK OFFICE
CERTIFICATE OF CORRECTION

PATENT NO. : 5,489,681

DATED : February 6, 1996

INVENTOR(S) : Thomas B.K. LEE et al.

It is certified that error appears in the above-identified patent and that said Letters Patent is hereby corrected as shown below:

On the title page, item [54] and column 1, line 3:

In the Title, "4-PHENYL-1,3-BENZODIAZEPINS" should read -- 4-PHENYL-1,3-BENZODIAZEPINES AND PRECURSORS THEREOF --

In the Abstract, line 10, "fore" should read --form--.

In claim 1, column 7, line 32,
"N-[2-(2-methylamino-2-phenym-" should read
-- N-[2-(2-methylamino-2-phenyl- --

In claim 1, column 7, line 36,
"N-methyl-2-amino-a-phenylphenethy-" should read
-- N-methyl-2-amino-α-phenylphenethyl- --

In claim 7, column 8, line 43, between formula (VI) and (VII), insert --or--

Signed and Sealed this

Fourteenth Day of May, 1996

Attest:

BRUCE LEHMAN

*Attesting Officer*        *Commissioner of Patents and Trademarks*